United States Patent

Suschitzky et al.

[11] 3,966,783
[45] June 29, 1976

[54] COMPOUNDS

[75] Inventors: John Louis Suschitzky; David Rutherford, both of Loughborough, England

[73] Assignee: Fisons Limited, London, England

[22] Filed: Nov. 11, 1974

[21] Appl. No.: 522,593

[30] Foreign Application Priority Data
Nov. 21, 1973   United Kingdom............... 54003/73
July 17, 1974   United Kingdom............... 31608/74

[52] U.S. Cl. ........................ 260/439 CY; 424/295
[51] Int. Cl.² ......................................... C07F 15/02
[58] Field of Search ........................... 260/439 CY

[56] References Cited
UNITED STATES PATENTS

| | | | |
|---|---|---|---|
| 2,810,737 | 10/1957 | Haven ........................ | 260/439 CY |
| 2,875,223 | 2/1959 | Pedersen et al.............. | 260/439 CY |
| 2,988,562 | 6/1961 | Weinmayr..................... | 260/439 CY |
| 3,078,291 | 2/1963 | Stephenson .................. | 260/439 CY |

OTHER PUBLICATIONS

Rosenblum, Chemistry of the Iron Group Metallocenes, Intersc. Publ., John Wiley & Sons, N.Y., PT1, pp. 91–93, 115–119, (1965).
Nesmeyanov et al., English Translation of Bulletin of the Academy of Science of USSR, No. 5, pp. 647–649, (1957).
House, Modern Synthetic Reactions, 2nd Ed., W. A. Benjamin, Inc. Cal., pp. 209–213, (1972).

*Primary Examiner*—Helen M. S. Sneed
*Attorney, Agent, or Firm*—Merriam, Marshall, Shapiro & Klose

[57] ABSTRACT

There are described compounds of formula I,

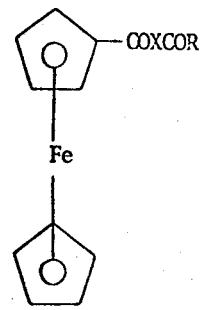

in which X is a saturated hydrocarbon group containing from 2 to 10 carbon atoms inclusive, and
R is alkyl, phenyl, or phenyl substituted by one or more halogen or alkyl groups.

There are also described processes for making the compounds and haematinic compositions containing them.

7 Claims, No Drawings

COMPOUNDS

This invention relates to new compounds, a method for their preparation and compositions containing them.

According to our invention we provide compounds of formula I,

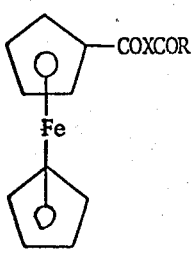

I in which X is a saturated hydrocarbon group containing from 2 to 10 carbon atoms inclusive, and
R is alkyl, phenyl, or phenyl substituted by one or more halogen or alkyl groups.

According to our invention we also provide a process for the production of a compound of formula I, which comprises a. reacting ferrocene with a compound of formula II, RxXCOR  II in which Rx is —CN, —COOH or an acid halide or anhydride thereof, and
R is as defined above, b. producing a compound of formula I in which R is phenyl, or phenyl substituted by up to five halogen or alkyl groups,
by reacting a compound of formula III,

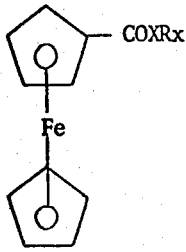

III in which, X and Rx are as defined above,
with benzene or benzene substituted by up to five halogen or alkyl groups, or c. producing a compound of formula Ia,

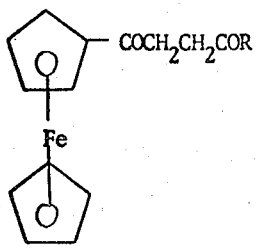

Ia in which R is as defined above,
by reductive hydrolysis of a compound of formula IV,

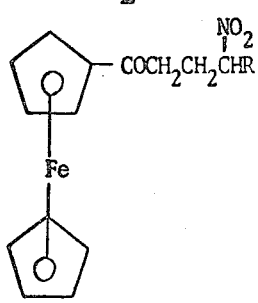

IV in which R is as defined above.

The reaction of both process (a) and process (b) may be carried out in a solvent which is inert under the reaction conditions, for example methylene chloride. The reaction is preferably carried out under Friedel-Crafts reaction conditions, for example in the presence of a Lewis acid such as aluminum chloride. The reaction is preferably carried out at a temperature of from about −25° to 0°C. The anhydride may be a symetrical anhydride or may be a mixed anhydride preferably of such a type that it will cleave preferentially to give the desired product. Examples of suitable acids from which the mixed anhydride may be derived are acetic, benzylic and trifluoroacetic acid. When the group Rx is —CN the product will be an imine which will be hydrolysed to the desired compound. We prefer the group Rx to be an acid halide group.

When the reaction is carried out at higher temperatures we have found than an increasing proportion of an isomeric impurity is produced. The compound of formula I may be isolated from this impurity using conventional techniques, e.g. crystallisation from suitable solvents such as ethyl acetate, or chromatography on an inert medium such as silica gel using organic eluents such as toluene or petroleum ether/ethyl acetate mixtures.

The reductive hydrolysis of process (c) may be carried out using, for example, aqueous titanium trichloride under an inert gas, e.g. nitrogen. The reaction may be carried out at a temperature of from about 5° to 50°C. The reaction involves reduction of the nitro group to an imine group which is then hydrolysed to a carbonyl oxygen atom.

Compounds of formula II and III are either known or may be made from known compounds using conventional techniques known per se.

Compounds of formula IV may be made by reaction of a compound of formula V,

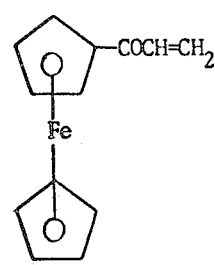

V with a compound of formula VI,

RCH$_2$NO$_2$  VI in which R is as defined above. The reaction may conveniently be carried out at room temperature, preferably in the presence of benzyl trimethyl ammonium hydroxide.

The compounds according to the present invention are useful because they possess pharmacological activity in animals. In particular, the compounds are useful as haematinics (as is shown by the rapid correction of iron deficiency anaemia, as determined by following haemoglobin regeneration, in anaemic rats to which the compounds have been administered orally, Laurence and Bacharach, Evaluation of Drug Activities - Pharmacometrics, Academic Press, New York, 1964 page 563) and are useful in the treatment of iron deficiency in man and other animals e.g. pigs, horses and cattle. The compounds are particularly useful for the treatment of iron deficiency anaemia in women. A substantial proportion of the dose administered to rats is transformed into physiologically acceptable iron stores (ferritin) and is retained in organs such as the liver. The degree of storage may be determined by measuring non-haem iron in the liver by the method of Torrance and Bothwell — South African Journal of Medical Science 1962, Volume 32 page 9. The compounds are particularly indicated for oral administration.

For the above mentioned use, the dosage administered will, of course, vary depending upon the compound employed, mode of administration and treatment desired. However, in general, satisfactory results are obtained when administered orally at a daily dosage of from about 1 milligram to 250 milligrams active ingredient per kilogram of animal body weight, preferably given 1 to 3 times a day, or in sustained release form. For man the total daily dosage is in the range of from about 50 milligrams to about 2,000 milligrams active ingredient, and unit dosage forms suitable for oral or parenteral administration comprise from about 20 to about 2,000 milligrams of the active ingredient.

The compounds according to the invention may be formulated into pharmaceutical compositions with pharmaceutically acceptable adjuvants, carriers or diluents. The nature of the adjuvant, carrier or diluent will depend in part on the intended mode of administration of the composition. Examples of suitable adjuvants, carriers and diluents are: for tablets and dragees lactose, starch, talc, stearic acid or an effervescent couple; for capsules — tartaric acid or lactose; for orally administered solutions or suspensions and for injectable solutions — water, alcohols, glycerin or vegetable oils; and for suppositories — natural or hardened oils or waxes. The compounds may also be formulated as a paste, granule, chewable gum or tablet, jelly, drinkable ampoule and/or in combination with a human or animal feedstuff, e.g. bread. In addition, the compositions may also include other pharmacologically active components such as Vitamin B12, Vitamin C (and/or other vitamins), an analgesic, e.g. aspirin, an anthelmintic, or folic acid. The composition may also contain suitable preserving, stabilising and wetting agents, solubilizers and sweetening and colouring agents and flavourings. If desired, the composition may be formulated in sustained release form or in enteric coated form. Compositions for oral administration are preferred.

The compounds of this invention possess pharmacological properties of an order not demonstrated by similar known compounds.

The group —X— may be a group —$(CH_2)_n$— in which n is a whole number from 2 to 6 inclusive. We prefer n to be 5. Alternatively the group —X— may be a branched chain alkyl group, e.g. a tetramethyl ethane or a —$CH(CH_3)$—$(CH_2)_4$— group. As a further alternative the group X may contain a cycloalkane group, e.g. a cyclobutane, or a cyclohexane group. When R is alkyl we prefer alkyl C 1 to 6, e.g. methyl or butyl. When R is phenyl substituted by halogen or alkyl we prefer mono- or tri-substitution. We prefer the halogen to be chlorine or fluorine. When R is phenyl substituted by alkyl we prefer the alkyl to contain 1 to 10, and more preferably 1 to 6 carbon atoms.

Some of the compounds of formula I may exist in optically active form and we therefore provide the individual isomers and mixtures, including racemic mixtures, thereof. The compounds of formula I may also exist in the enol form, but throughout this specification the keto form has been used to indicate both enol and keto forms.

The invention is illustrated, but in no way limited by the following Examples in which the temperatures are in degrees centigrade.

EXAMPLE 1

1-Ferrocenyl-6-phenylhexa-1,6-dione a. 6-Oxo-6-phenylhexanoyl chloride

6-Oxo-6-phenyl hexanoic acid (10.3g; 50 mmole), thionyl chloride (25 ml) and dry benzene (150 ml) were heated under reflux for 3 hours. The reagent and solvent were removed on the rotary evaporator. A further 100 ml of benzene was added and the solution again evaporated under reduced pressure (to remove last traces of thionyl chloride). The quantitatively formed, analytically pure brown solid (mp 53°–6°) was used directly in the Friedel-Crafts acylation of step (b).

b. 1-Ferrocenyl-6-phenylhexa-1,6-dione

The 6-Oxo-6-phenylhexanoyl chloride product of step (a) was stirred at −20° (carbon tetrachloride/dry ice bath) and ferrocene (9.3g; 50 mmole) was added, followed by aluminium chloride (6.7g; 50 mmole), the latter over 90 min. Stirring at −20° was continued for another 90 minutes and water (250 ml) was added slowly with rapid stirring to the still cooled solution. The organic layer was run off, and the aqueous layer extracted with methylene chloride (100 ml). The combined organic layers were washed with water (3 × 200 ml), dried (sodium sulphate) to yield a brown oil which crystallised on trituration with cyclohexane. Two recrystallisations from cyclohexane gave a yellow powder of almost pure product (4.5g) m.p. 69°–71°C.

EXAMPLE 2

5-(4-Chlorobenzoyl)pentanoylferrocene 5-(4-Chlorobenzoyl)pentanoic acid (9.6g) was dissolved in dry toluene (80 ml) and thionyl chloride (10 ml) added. The reaction mixture was heated to reflux for 4 hours. The excess toluene and thionyl chloride were removed in vacuo, more toluene was added and again removed in vacuo affording 5-(4-chlorobenzoyl)-pentanoyl chloride (10.4g 100%) as a pale brown solid.

5-(4-Chlorobenzoyl)pentanoyl chloride (5.2g — 0.02 mole) — prepared as described above — and ferrocene (3.75g — 0.02 mole) were dissolved in dry dichloromethane (100 ml) and cooled to −20°C. Aluminium chloride (2.70g — 0.02 mole) was added, with stirring, over a period of one-half hour and stirring was continued at −20°C for 1½ hours. The reaction mixture was poured into water (300 ml) acidified with 2N hydrochloric acid (20 ml). The dichloromethane layer was separated and the aqueous layer extracted with chloroform (3 × 100 ml). The combined organic extracts were washed with water (100 ml), saturated aqueous sodium bicarbonate solution (100 ml) and water (100 ml), dried ($MgSO_4$) and concentrated affording the crude product (9.8g) as a brown solid. Recrystallisation from petroleum ether (bp 60°–80°) afforded the title compound (3.23g — 40%) mp 103°–6°.

EXAMPLE 3

2-Methyl-6-benzoylhexanoylferrocene

2-Methyl-6-benzoylhexanoic acid (15.1g; 0.065 mole) in toluene (100 ml) was heated under reflux for 2 hours with thionyl chloride (7.7g; 0.065 mole). The toluene was removed by evaporation under reduced pressure to yield the acid chloride as a pale brown oil which was used directly in the synthesis of the ferrocene derivative.

2-Methyl-6-benzoylhexanoylchloride (assumed to be 0.065 mole) and ferrocene (12.0g; 0.065 mole) in dry methylene chloride (500 ml) were stirred at 0.5° and aluminium chloride (17g; 0.13 mole) was added. The mixture was stirred for 30 mins at 0°–5°, then ice was added slowly and the organic fraction separated. The aqueous fraction was extracted with chloroform and the combined organic fractions were washed with water and dried (magnesium sulphate) to yield a brown oil which was recrystallised from petroleum ether to yield orange needles of pure 2-methyl-6-benzoylhexanoylferrocene mp 75° (40%).

EXAMPLE 4

1-Mesitoyl-2-ferrocenoylcyclobutane

1-Mesityl-cyclobutan-2-oic acid (0.1 mole; 25.5g) in dry methylene chloride (200 ml) was stirred at 0° for 5 hrs with oxalylchloride (20g; 0.17 mole). The methylene chloride and excess reagent were removed by evaporation under reduced pressure at room temperature to yield the acid chloride as a yellow oil which was used directly in the synthesis of the ferrocene derivative.

1-Mesityl-cyclobutan-2-oic acid chloride (assumed to be 0.1 mole) and ferrocene (18.6g; 0.1 mole) in dry methylene chloride (200 ml) were stirred at 0°–5° and aluminium chloride (20g; 0.15 mole) was added. The mixture was stirred at 0°–5° for 30 minutes and at room temperature for 1 hr; ice was added slowly and the organic fraction was separated. The aqueous fraction was extracted with chloroform, and the combined organic fractions were washed with water and dried (magnesium sulphate). The solvent was evaporated under reduced pressure to yield a red oil which was purified by column chromatography on silica using 10:1 petroleum ether/ethyl acetate as eluent. The major band gave a red oil which was recrystallised from petroleum ether to give orange crystals of 1-mesityl-2-ferrocenoyl cyclobutane mp 113°–114.5° (20%).

EXAMPLE 5

4-Benzoylbutyrylferrocene

4-Benzoylbutyric acid (1.0g; 0.005 mole) in dry methylene chloride (20 ml) was stirred at 0° for 1 hr and room temperature for 1 hr with oxalyl chloride (excess). The methylene chloride and excess reagent were removed by evaporation under reduced pressure at room temperature to yield the acid chloride as a yellow solid which was used directly in the synthesis of the ferrocene derivative.

4-Benzoylbutryl chloride (assumed to be 0.005 mole) and ferrocene (0.97g; 0.005 mole) in dry methylene chloride (25 ml) were stirred at 0°–5° and aluminium chloride (1.04g; 0.011 mole) was added. The mixture was stirred at room temperature for 30 minutes, ice was added slowly and the organic fraction was separated. The aqueous fraction was extracted with chloroform and the combined organic fractions were washed with water, dried (magnesium sulphate) and evaporated. The resulting oil was purified by column chromatography on silica using 9:1 petroleum ether: ethyl acetate as eluent to yield a yellow solid which was recrystallised from petroleum ether to yield pure 4-benzoylbutyrylferrocene mp 96° (3%).

EXAMPLE 6

7,7-Dimethyl-6-oxooctanoylferrocene 7,7-Dimethyloctanoic acid (18.6g; 0.1 mole) in toluene (200 ml) was heated under reflux for 4 hrs with thionyl chloride (16 ml; excess). The toluene and reagent were removed on the rotary evaporator to yield the acid chloride as a brown oil which was used directly in the synthesis of the ferrocene derivative.

7,7-Dimethyl-6-oxooctanoylchloride (assumed to be 0.1 mole from the above preparation) in methylene chloride (200 ml) and ferrocene (18.6g; 0.1 mole) were stirred at −20°C and aluminium chloride (13.4g; 0.1 mole) was added over 1 hr. After stirring for a further 2 hrs at −20°C, the reaction had almost gone to completion. Water was added and the organic layer separated. The aqueous layer was extracted with methylene chloride and the combined organic layers were washed with saturated sodium bicarbonate and water, and dried (sodium sulphate) to yield a brown oil which crystallised on addition of petroleum ether and was recrystallised from petroleum ether: cyclohexane (750 ml of 1:1) to yield 7,7-dimethyl-6-oxo-octanoylferrocene as an orange-brown solid. mp 90°–2° (65.3%).

EXAMPLE 7

Mesitoylbutyrylferrocene

Ferrocenoyl butyric acid (12.6g; 42 m mole) in methylene chloride (80 ml) were stirred at 0° and a solution of oxalylchloride (21 ml) in methylene chloride (80 ml) was added over one-half hour. Stirring at 0° was continued for 40 mins and then at room temperature for 10 minutes. The acid chloride was obtained as a brown oil on evaporation of the solution and was used without purification.

Ferrocenoylbutyrylchloride (obtained from above and assumed to be 40 m mole) was dissolved in mesitylene (150 ml) and aluminium chloride (5.34g; 40 m mole added). The mixture was stirred at 80° for 40 minutes. The tan-like material which was insoluble in mesitylene was separated, taken up in benzene, and washed with water, 2N HCl, saturated sodium bicarbonate and water, and dried (sodium sulphate) to yield a dark oil which was recrystallised from petroleum ether (bp 40°–60°) to yield 2.05g (12.2%) of pure mesitoylbutyryl ferrocene as a brown soild mp 75°–6°.

EXAMPLE 8

7-Oxooctanoylferrocene

7-Oxooctanoic acid (15.8g; 0.1 mole) in dry toluene (200 ml) was stirred at −10° for 3 hrs with oxalyl chloride (50 ml). Removal of the solvent gave NMR pure acid chloride used directly in the synthesis of the ferrocene derivative.

The acid chloride (assumed 0.1 mole from above) in methylene chloride (250 ml) and ferrocene (18.6g; 0.1 mole) were stirred at −20° and aluminium chloride (13.4g; 0.1 mole) was added over 1 hour. The mixture was worked up (as described in the preparation of 7,7-Dimethyl-6-oxooctanoylferrocene in Example 6) to yield a brown oil which was chromatographed on silica. 7½% ethyl acetate in toluene eluted an unidentified product. 25% ethyl acetate in toluene yielded moderately pure 7-oxooctanoyl ferrocene which was recrystallised to give the pure compound (5.0g; 15%) mp 77°–8°.

EXAMPLE 9

7-Oxo-7-phenylheptanoyl ferrocene

7-Oxo-7-phenylheptanoyl chloride (0.75 mole) was prepared from 7-oxo-7-phenylheptanoic acid, using a process analogous to that described in Example 6.

The crude acid chloride (an oil assumed 0.75 mole) and ferrocene (14.0g; 0.75 mole) was stirred at −20° in methylene chloride (2½ l) and aluminium chloride (100.1g; 0.75 mole) was added over 1 hr. The mixture was stirred for 3 hours at −20° and then worked up as described in Example 6 to yield a brown oil which was dissolved in ether and cooled to −20° to yield 41.9g of moderately pure product. A further recrystallisation from ether gave pure 7-oxo-7-phenylheptanoyl ferrocene in three crops (total 38.9g; 12%) mp 67°–9°.

EXAMPLE 10

4-Oxopentanoyl ferrocene

Nitroethane (3g; 40 m mole) in ethanol (120 ml) was heated under reflux and under nitrogen for 10 minutes with benzyltrimethyl ammonium hydroxide (1 ml) and then cooled to room temperature. Acryloylferrocene (6.5g; 27.1 mole) was then added and the solution was stirred for 1 hour and then filtered. The filtrate was concentrated on the rotary evaporator, then poured into water and extracted with chloroform. The organic extract was washed (water) and dried (sodium sulphate) to give a brown solid which was recrystallised from cyclohexane/petroleum ether to give 4-nitropentanoyl ferrocene (1.65g; 19.2%) mp 79°–80°.

The nitro compound (315 mg; 1 m mole) in glyme (5 ml) was treated with titanium trichloride (4 m mole) in water (5 ml) under $N_2$ with stirring at room temperature. After 2 days a further 4 m mole of $TiCl_3$ was added and stirring was continued for 24 hrs. The product was poured into chloroform (50 ml) and saturated sodium bicarbonate was added until precipitation of titanium dioxide was complete. The two layers were filtered through 'Hiflo' and the chloroform layer was washed with sodium bicarbonate solution, water and dried (sodium sulphate) to yield an oil which was chromatographed on silica to yield starting material (eluted with 5% ethyl acetate/toluene) and 4-oxopentanoyl ferrocene (30 mg; 10.6%) NMR 8, 4.75 (t, 2H); 4.44 (t, 2H); 4.21 (S, 5H); 3.1 2.6 ($A_2B_2$, 4H); 2.21 (S, 3H).

EXAMPLE 11

6-Oxo-heptanoylferrocene a. 6-Oxo-heptanoyl chloride

6-Oxo-heptanoic acid (20.1g; 0.14 mole), thionyl chloride (18.3g; 11.2 ml; 0.154 mole) and dry benzene (300 ml) together with dimethylformamide (three drops) were stirred at room temperature for 22 hours. The halogenating reagent and benzene were removed on the rotary evaporator. A further 100 ml of benzene was added and the solution was again evaporated under reduced pressure (to remove last traces of thionyl chloride). The quantitatively formed liquid acid chloride was used directly in step (b).

b. 6-Oxo-heptanoyl ferrocene

Ferrocene (26g; 0.14 mole) was dissolved in dichloromethane (500 ml) and stirred at −35° (1,2-dichloroethane/dry ice bath). 6-Oxo-heptanoyl chloride from step (a) was added followed by aluminium chloride (18.7g; 0.14 moles) over 30 minutes. Stirring at −35° was continued for another 2 hours and the mixture was poured into ice/water (1 kg). The dichloromethane layer was separated, washed with water (3 × 600 ml), dried over sodium sulphate and concentrated under vacuum, giving a red oil. The desired product was isolated by column chromatography using 9:1 toluene-:ethyl acetate as eluent on silica. Recrystallisation of the orange solid from petroleum ether (bp 60–80) afforded the pure compound (3.2g; 73%) mp 70°–71°.

EXAMPLE 12

5-(2-Fluorobenzoyl)pentanoylferrocene o-Fluorobenzoylvaleric acid (20g; 0.08 mole) in toluene (150 ml) was heated under reflux for 1 hour with thionyl chloride (6g; 0.1 mole). The toluene and excess reagent were evaporated off under vacuum to yield a brown oil which was used directly in the synthesis of the ferrocene derivative.

The acid chloride (assumed to be 0.08 mole, from the above preparation) and ferrocene (15g; 0.08 mole) in methylene chloride (500 ml) were stirred at 0°–5°, and aluminium chloride (22g; 0.16 mole) was added slowly. The mixture was stirred for 1 hour at 0°–5° after which water was added and the organic layer was separated. The aqueous layer was extracted with methylene chloride and the combined organic fractions were washed with water and dried (magnesium sulphate) to yield on evaporation a red oil, which was chromatographed on silica and eluted with 9:1 petroleum ether-:ethyl acetate. The product was recrystallised from petroleum ether to yield 3.2g (10%) pure 5-(2-fluorobenzoyl)pentanoylferrocene as orange crystals, mp 70°–71°.

We claim:

1. A compound of formula I,

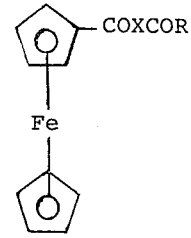

I in which X is a bivalent saturated hydrocarbon group containing from 2 to 10 carbon atoms inclusive, and R is $C_1$ to $C_6$ alkyl, phenyl, or phenyl substituted by one or more halogen or alkyl groups.

2. A compound according to claim 1, wherein X is a group —$(CH_2)_n$— in which $n$ is a whole number from 2 to 6 inclusive.

3. A compound according to claim 1 wherein X is a branched or cyclic unsaturated hydrocarbon group.

4. A compound according to claim 1 wherein R is phenyl mono- or tri- substituted by halogen or $C_1$ to $C_{10}$ alkyl.

5. A compound according to claim 4, wherein the halogen is chlorine or fluorine.

6. A compounding according to claim 1, which is 1-Ferrocenyl-6-penylhexa-1,6-dione; 5-(4-Chlorobenzoyl)pentanoylferrocene; 2-Methyl-6-benzoylhexanoylferrocene; 1-Mesitoyl-2-ferrocenoylcyclobutane; 4-Benzoylbutyrylferrocene; 7,7-Dimethyl-6-oxooctanoylferrocene; Mesitoylbutyrylferrocene; 7-Oxooctanoylferrocene; 7-Oxo-7-phenylheptanoyl ferrocene; 4-Oxopentanoyl ferrocene; 6-Oxo-heptanoylferrocene; or 5-(2-Fluorobenzoyl)pentanoylferrocene.

7. A compound of formula IV,

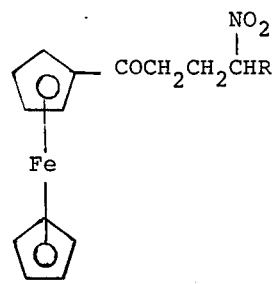

in which R is $C_1$ to $C_6$ alkyl, phenyl, or phenyl substituted by one or more halogen or alkyl groups.

* * * * *